United States Patent
Yukawa et al.

(10) Patent No.: US 9,535,006 B2
(45) Date of Patent: Jan. 3, 2017

(54) SEMICONDUCTOR NANOPARTICLES AND FLUORESCENT PROBE FOR BIOLOGICAL LABELING

(71) Applicant: NATIONAL UNIVERSITY CORPORATION NAGOYA UNIVERSITY, Nagoya-shi, Aichi-ken (JP)

(72) Inventors: Hiroshi Yukawa, Nagoya (JP); Hiroyasu Nishi, Tokyo (JP); Tsukasa Torimoto, Nagoya (JP); Yoshinobu Baba, Nagoya (JP)

(73) Assignee: NATIONAL UNIVERSITY CORPORATION NAGOYA UNIVERSITY, Aichi-ken (JP)

( * ) Notice: Subject to any disclaimer, the term of this patent is extended or adjusted under 35 U.S.C. 154(b) by 275 days.

(21) Appl. No.: 14/056,329

(22) Filed: Oct. 17, 2013

(65) Prior Publication Data

US 2014/0284528 A1 Sep. 25, 2014

(30) Foreign Application Priority Data

Mar. 22, 2013 (JP) ................ 2013-060365

(51) Int. Cl.
*H01B 1/10* (2006.01)
*G01N 33/00* (2006.01)
(Continued)

(52) U.S. Cl.
CPC ............ *G01N 21/643* (2013.01); *B82Y 15/00* (2013.01); *C09K 11/54* (2013.01); *G01N 33/582* (2013.01); *H01B 1/10* (2013.01)

(58) Field of Classification Search
CPC .......... H01B 1/10; C09K 11/54; C09K 11/56; C09K 11/58; G01N 33/582; G01N 21/6428; G01N 21/6486; C12Q 2563/107; B82Y 15/00
See application file for complete search history.

(56) References Cited

U.S. PATENT DOCUMENTS

2008/0099728 A1  5/2008  Jin et al.

FOREIGN PATENT DOCUMENTS

| JP | A-2009-215465 | 9/2009 |
| JP | A-2010-31115 | 2/2010 |
| KR | 943993 B1 * | 2/2010 |

OTHER PUBLICATIONS

Sheng et al "Synthesis of AIZS@SiO2 core-shell nanoparticles for cellular imaging applications", J. Mater. Chem., 2012, 22, 1290-1296.*

(Continued)

*Primary Examiner* — Mark Kopec
(74) *Attorney, Agent, or Firm* — Oliff PLC (57) ABSTRACT

Semiconductor nanoparticles of the present invention are particles each having a core-shell structure that includes a core and a shell surrounding the core. The core includes $(AgIn)_x Zn_{2(1-x)} S_2$ ($0.4 \le x \le 0.95$ holds). The shell includes ZnS or ZnO, and the semiconductor nanoparticles each have at least one hydrophilic functional group on a surface of the shell. As the hydrophilic functional group, for example, a carboxyl group or a sulfo group may be mentioned. Since having a low toxicity and a high emission quantum yield, the semiconductor nanoparticles as described above may be used for a fluorescent probe for biological labeling.

16 Claims, 5 Drawing Sheets

(51) Int. Cl.
  *G01N 21/00*   (2006.01)
  *G01N 21/64*   (2006.01)
  *B82Y 15/00*   (2011.01)
  *G01N 33/58*   (2006.01)
  *C09K 11/54*   (2006.01)

(56) References Cited

OTHER PUBLICATIONS

Torimoto et al "Remarkable photoluminescence enhancement of ZnS—AgInS2 solid solution nanoparticles by post synthesis treatment", Chem. Commun. 2010, 46, 2082-2084.*

English language machine translation of KR 10-0943993 (pub date Feb. 2010).*

Kameyama et al., "Photoluminescence Enhancement of ZnS—AgInS$_2$ Solid Solution Nanoparticles layer-by-layer-assembled in Inorganic Multilayer Thin Films," *Chemistry Letters*, 2008, pp. 700-701, vol. 37, No. 7.

Dai et al., "One-Pot Synthesis of Water-Soluble Nanoparticles of ZnS—AgInS$_2$ Solid Solution with Controllable Photoluminescence," *Electrochemistry*, 2011, pp. 790-792, vol. 79, No. 10.

Yukawa et al., "Quantum dots labeling using octa-arginine peptides for imaging of adipose tissue-derived stem cells," *Biomaterials*, 2010, pp. 4094-4103, vol. 31.

Yukawa et al., "Monitoring transplanted adipose tissue-derived stem cells combined with heparin in the liver by fluorescence imaging using quantum dots," *Biomaterials*, 2012, pp. 2177-2186, vol. 33.

Tiwari et al., "Synthesis and Characterization of Anti-HER2 Antibody Conjugated CdSe/CdZnS Quantum Dots for Fluorescence Imaging of Breast Cancer Cells," *Sensors*, Nov. 19, 2009, pp. 9332-9354, vol. 9.

Jin et al., "A quantum dot-based ratiometric pH sensor," *Chem. Commun.*, Mar. 4, 2010, pp. 2408-2410, vol. 46.

Jin et al., "$Gd^{3+}$-functionalized near-infrared quantum dots for in vivo dual modal (fluorescence/magnetic resonance) imaging," *Chem. Commun.*, 2008, pp. 5764-5766.

Jin et al., "Preparation and Characterization of Highly Fluorescent, Glutathione-coated Near Infrared Quantum Dots for in Vivo Fluorescence Imaging," *Int. J. Mol. Sci.*, Oct. 29, 2008, pp. 2044-2061, vol. 9.

Torimoto et al., "Facile Synthesis of ZnS—AgInS$_2$ Solid Solution Nanoparticles for a Color-Adjustable Luminophore," *J. Am. Chem. Soc.*, Sep. 21, 2007, pp. 12388-12389, vol. 129.

Torimoto et al., "Remarkable photoluminescence enhancement of ZnS—AgInS$_2$ solid solution nanoparticles by post-synthesis treatment," *Chem. Commun.*, Feb. 19, 2010, pp. 2082-2084, vol. 46.

Zhou et al., "A chelating dendritic ligand capped quantum dot: preparation, surface passivation, bioconjugation and specific DNA detection," *Nanoscale*, 2011, pp. 201-211, vol. 3.

* cited by examiner

ZnS-ZAIS-COOH (250 nM)

FIG. 7

ZnS-ZAIS-SO3H (250 nM)

SEMICONDUCTOR NANOPARTICLES AND FLUORESCENT PROBE FOR BIOLOGICAL LABELING

BACKGROUND OF THE INVENTION

1. Field of the Invention

The present invention relates to semiconductor nanoparticles and a fluorescent probe for biological labeling.

2. Description of the Related Art

A cell imaging technique is an important technique to investigate cell kinetics. Heretofore, cell imaging using various types of dyes has been developed, and in recent years, cell imaging using quantum dots which simultaneously have a high emission quantum yield, a high absorption coefficient, a wide absorption region, and a high durability has attracted attention. However, in imaging using quantum dots, particles containing cadmium (Cd), which may have some toxicity, are used in many cases, and hence development of high-brightness quantum dots using an alternative element having a low toxicity has been desired. In the circumstances as described above, for example, PTL 1 and NPLs 1, 2 have disclosed water-soluble semiconductor nanoparticles in which sulfo groups ($-SO_3H$) are introduced in semiconductor nanoparticles formed of a ZnS—AgInS$_2$ solid solution (ZAIS). Since nanoparticles become water soluble when sulfo groups are introduced therein and are hence likely to be incorporated into cells, the nanoparticles are expected to be used as quantum dots for cell imaging.

CITATION LIST

Patent Literature

[PTL 1] JP 2009-215465 A (Examples 1 and 2)

Non Patent Literature

[NPL 1] Chemistry Lett. 2008, vol. 37, p 700-701
[NPL 2] Electrochemistry 2011, vol. 79, p 790-792

SUMMARY OF THE INVENTION

Technical Problem

However, as disclosed in NPL 2, the emission quantum yield of semiconductor nanoparticles obtained when sulfo groups are introduced in ZAIS is only 8%, and this remarkable decrease from the emission quantum yield (approximately 20%) before sulfo groups are introduced in ZAIS has been a problem. In addition, although semiconductor nanoparticles each having a core-shell structure in which ZAIS is used as a core and ZnS is used as a shell has also been known (for example, the patent document JP 2010-31115 A), concrete techniques using such semiconductor nanoparticles for cell imaging have not been reported as of today.

The present invention was made to overcome the problems described above, and a primary object of the present invention is to provide semiconductor nanoparticles having a low toxicity and a high emission quantum yield.

Solution to Problem

In order to achieve the above object, the present inventors examined the properties of semiconductor nanoparticles each having a core-shell structure in which ZAIS is used as the core and ZnS is used as the shell after the surface of the shell was modified with various types of molecules. As a result, the present inventors discovered that nanoparticles modified with molecules having hydrophilic functional groups are useful as quantum dots for cell imaging, and hence the present invention was completed.

That is, the semiconductor nanoparticles of the present invention are semiconductor nanoparticles each having a core-shell structure formed of a core and a shell surrounding the core, the core includes $(AgIn)_xZn_{2(1-x)}S_2$ ($0.4 \leq x \leq 0.95$ holds), the shell includes ZnS or ZnO, and the semiconductor nanoparticles each have at least one hydrophilic functional group on the surface of the shell.

In addition, a fluorescent probe for biological labeling of the present invention includes the semiconductor nanoparticles described above.

Advantageous Effects of the Invention

The semiconductor nanoparticles of the present invention have a low toxicity and a high emission quantum yield. Hence, the semiconductor nanoparticles of the present invention are suitable as quantum dots for cell imaging and have a high utility value as a fluorescent probe for biological labeling.

DESCRIPTION OF PREFERRED EMBODIMENTS

Semiconductor nanoparticles of the present invention are semiconductor nanoparticles each having a core-shell structure that includes a core and a shell surrounding the core, the core includes $(AgIn)_xZn_{2(1-x)}S_2$ ($0.4 \leq x \leq 0.95$ holds), the shell includes ZnS or ZnO, and the semiconductor nanoparticles each have at least one hydrophilic functional group on the surface of the shell.

In the semiconductor nanoparticles of the present invention, the core includes $(AgIn)_xZn_{2(1-x)}S_2$, and $0.4 \leq x \leq 0.95$ holds. The reason x is set in the range described above is that the emission quantum yield is relatively high. In addition, $0.8 \leq x \leq 0.9$ is preferably satisfied. The reason for this is that in this case, besides a relatively high emission quantum yield, since the emission wavelength is 700 to 900 nm and is in a biological spectroscopic window, the in vivo dynamic behavior can be effectively investigated.

In the semiconductor nanoparticles of the present invention, the shell includes ZnS or ZnO. Between the above two, ZnS is preferable. In order to improve the emission quantum yield, the thickness of the shell is preferably more than 0 and not more than 50 nm, more preferably more than 0 and not more than 1.0 nm, and even more preferably more than 0 and not more than 0.5 nm.

The semiconductor nanoparticles of the present invention each have at least one hydrophilic functional group on the surface of the shell. As the hydrophilic functional group, a carboxyl group ($-CO_2H$) and its salt, a sulfo group ($-SO_3H$) and its salt, a quarternary ammonium salt, and the like may be mentioned by way of example. Among these, a carboxyl group, a sulfo group, and salts thereof are preferable, and in consideration of incorporation of the functional group into biological bodies, a carboxyl group and its salt are more preferable. As the salt, for example, an alkali metal salt and an alkaline earth metal salt may be mentioned. In addition, a bifunctional molecule having the above-described hydrophilic functional group (first functional group) and a functional group (second functional group) which can be bonded to the surface of the shell is preferably bonded to the surface of the shell by the second functional group. In addition, although the bonding mode to the surface of the shell is not particularly limited, chemical bonds, such as a covalent bond, an ionic bond, a coordinate bond, a hydrogen bond, and a van der Waals bond may be mentioned. The first functional group is the hydrophilic functional group as described above. As the second functional group, for example, a functional group containing a sulfur atom and a functional group containing a nitrogen atom may be mentioned. As the functional group containing a sulfur atom, for example, a mercapto group; a group having a disulfide bond, such as an alkyldithio group; a group having a sulfide bond, such as an alkylthio group; a pyridylthio group; or a dithiocarboyl group may be mentioned. As the functional group containing a nitrogen atom, a functional group containing a nitrogen atom, such as an imino group, an amide group, an imide group, or a pyridyl group, may be mentioned. As the bifunctional molecule, for example, a molecule having a structure in which the first functional group and the second functional group are connected by a hydrocarbon group or an ether group is preferable. As a particular example of the bifunctional molecule, for example, 3-mercaptopropionic acid, 4-mercaptobutyric acid, 2-mercaptoethane sulfonic acid, or 3-mercaptopropane sulfonic acid may be mentioned.

The semiconductor nanoparticles of the present invention preferably have a particle diameter at which the quantum size effect is obtained, and in particular, the particle size of the semiconductor nanoparticles is preferably 100 nm or less, more preferably 50 nm or less, and even more preferably 20 nm or less.

Figure 1:
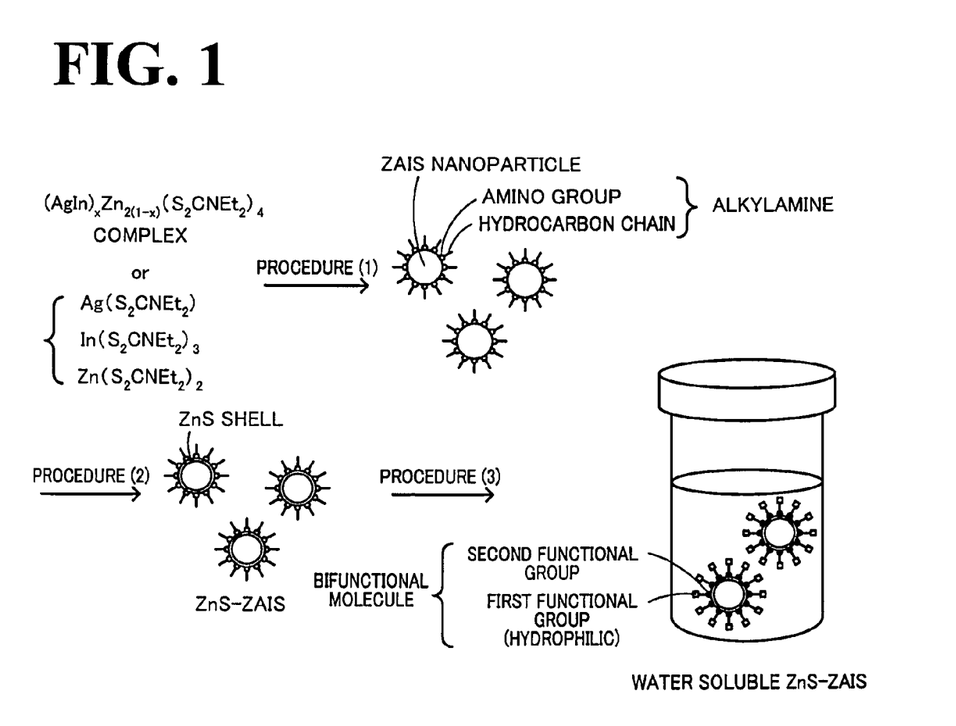
FIG. 1 is an explanation view showing one example of a synthetic procedure of semiconductor nanoparticles of the present invention.

The semiconductor nanoparticles of the present invention are synthesized, for example, by the following procedures (1) to (3) (see, FIG. 1). In this embodiment, the case in which the shell includes ZnS will be described.
(1) Nanoparticles of $(AgIn)_x Zn_{2(1-x)} S_2$ ($0.4 \leq x \leq 0.95$ holds) modified with an alkylamine, that is, ZAIS nanoparticles, are synthesized.
(2) By using the ZAIS nanoparticles as a raw material, ZnS—ZAIS having a core-shell structure modified with an alkylamine is synthesized. In this case, ZnS—ZAIS represents ZAIS nanoparticles coated with ZnS.
(3) By a ligand substitution method, the alkylamine of the ZnS—ZAIS modified with an alkylamine is substituted with molecules each having a hydrophilic functional group.

In the procedure (1), after an Ag salt, an In salt, a Zn salt, and a ligand containing sulfur as a coordinated element are mixed together to synthesize a complex, the complex thus obtained is heated to 100° C. to 300° C. and preferably 150° C. to 200° C., and the surface of a heated substance is modified with an alkylamine. As the individual salts, for example, a nitric acid salt, an acetic acid salt, and a sulfuric acid salt may be mentioned. Among these, a nitric acid salt is preferable. As the ligand containing sulfur as a coordinated element, for example, a dialkyldithiocarbamate salt, such as sodium diethyldithiocarbamate, a thiol, such as 1,2-bis(trifluoromethyl)ethylene-1,2-dithiol, and a thiocarboxylic acid amide, such as thioacetamide, may be mentioned. Among these, a dialkyldithiocarbamate salt is preferable. The mixing ratio between the individual salts may be determined in accordance with the value of x. As the alkylamine, an amine having a hydrocarbon group with 4 to 20 carbon atoms is preferable. In addition, when dialkyldithiocarbamate salts of Ag, In, and Zn are used as raw materials, since the ligand containing sulfur as a coordinated element is not required, after these three salts are mixed and heated, the surface of a heated substance may be modified with an alkylamine.

In the procedure (2), the ZAIS nanoparticles modified with the alkylamine are heated to 100° C. to 350° C. and preferably 150° C. to 250° C. with zinc acetate, thioacetamide, and an alkylamine. Accordingly, the surfaces of the ZAIS nanoparticles are coated with ZnS to form ZnS—ZAIS having a core-shell structure, and in addition, the surface of the shell is modified with the alkyl amine. The procedures (1) and (2) have been described in detail in the patent document JP 2010-31115 A.

In the procedure (3), the ZnS—ZAIS modified with the alkylamine is mixed and stirred with the above bifunctional molecules each having the first functional group and the second functional group, so that the alkylamine is substituted with the bifunctional molecules. The second functional group of the bifunctional molecule is bonded to the surface of the shell, and the first functional group, that is, the hydrophilic functional group, faces outside. The mixing and stirring may be performed at room temperature or by heating. As a solvent, a two phase system including an organic phase and an aqueous phase may be used, and in the case of the two phase system, a phase transfer catalyst may be added. The semiconductor nanoparticles of the present invention obtained by this reaction are water soluble.

A fluorescent probe for biological labeling of the present invention includes the semiconductor nanoparticles described above. This fluorescent probe has a low cell toxicity. In addition, when the value of x is adjusted so that emission occurs at a wavelength of 700 to 900 nm, the in vivo dynamic behavior can be investigated.

EXAMPLES

A. Synthesis of ZnS—ZAIS Modified with Molecules having Hydrophilic Functional Groups 1. Synthesis of ZAIS Nanoparticles Modified with Oleylamine Synthetic Example 1

In accordance with the procedure disclosed in J. Am. Chem. Soc. 2007, vol. 129, p 12388 to 12389, ZAIS nanoparticles were synthesized. As a precursor, $(AgIn)_x Zn_{2(1-x)} (S_2CN(C_2H_5)_2)_4$ having x of 0.85 was used.

Synthetic Example 2

ZAIS nanoparticles were synthesized as described below. $Ag(S_2CNEt_2)$ (13.6 mg), $In(S_2CNEt_2)_3$ (29.7 mg), and Zn(S$_2$CNEt$_2$)$_2$ (6.8 mg) were dispersed in oleylamine (3.0 ml) and were heated in a nitrogen atmosphere at 180° C. for 30 minutes. A solution obtained thereby was centrifuged at 4,000 rpm for 5 minutes so as to remove large particles as a precipitate, and after methanol was added to a supernatant, a mixture obtained thereby was centrifuged at 4,000 rpm for 5 minutes, so that ZAIS nanoparticles (x=0.85) were obtained as a precipitate.

2. Synthesis of ZnS—ZAIS

With reference to Chem. Commun. 2010, vol. 46, p 2082 to 2084, ZnS—ZAIS was synthesized as described below. All the ZAIS nanoparticles synthesized using the amounts and methods disclosed in (1) or (2) of the above 1, zinc acetate dihydrate (11.8 mg), and thioacetamide (4.0 mg) were dispersed in oleylamine (2.0 ml) and were then heated in a nitrogen atmosphere at 180° C. for 30 minutes. After a solution obtained thereby was filtrated with a syringe filter, methanol was added, and centrifugation was performed at 4,000 rpm for 5 minutes, so that ZnS—ZAIS was separated as a precipitate.

3. Synthesis of Zns—ZAIS (ZnS—ZAIS—COOH) Modified with Molecules having Carboxylic Groups With reference to Nanoscale 2011, vol. 3, p 201 to 211, ZnS—ZAIS—COOH was synthesized as described below. All the ZnS—ZAIS synthesized using the amounts and methods disclosed in the above 2. was dissolved in chloroform (1.0 mL) and was mixed with 3-mercaptopropionic acid (MPA) (100 mL) and an ethanol (1.0 mL) solution containing a methanol solution (730 μL) of tetramethyl ammonium hydroxide at a concentration of 25%. This reaction solution was heated in a nitrogen atmosphere at 70° C. for 5 hours. After the solvent was removed under reduced-pressure conditions, a crude product thus obtained was dissolved in ethanol, and chloroform was added thereto, followed by performing centrifugation at 4,000 rpm for 5 minutes, thereby separating particles as a precipitate. The cycle of the dissolution in ethanol, the addition of chloroform, and the centrifugation was performed several times, so that residual reagents were removed. The particles thus obtained were dried under reduced-pressure conditions and were then dissolved in ultrapure water, so that an aqueous solution of ZnS—ZAIS—COOH was obtained.

4. Synthesis of Zns—ZAIS (Zns—ZAIS—SO$_3$H) Modified with Molecules having Sulfo Groups Synthetic Example 1

In accordance with the procedure disclosed in Chem. Lett. 2008, vol. 37, p 700 to 701, ZnS—ZAIS—SO$_3$H was synthesized from the ZnS—ZAIS synthesized in the above 2.

Synthetic Example 2

With reference to Nanoscale 2011, vol. 3, p 201 to 211, ZnS—ZAIS—SO$_3$H was synthesized as described below. All the ZnS—ZAIS synthesized using the amounts and methods disclosed in the above 2. was dissolved in chloroform (1.0 mL) and was mixed with 2-mercaptoethane sodium sulfonate (MES) (164 mg) and an methanol (1.0 mL) solution containing a methanol solution (730 μL) of tetramethyl ammonium hydroxide at a concentration of 25%. This reaction solution was heated in a nitrogen atmosphere at 70° C. for 1.5 hours. After the solvent was removed under reduced-pressure conditions, a crude product thus obtained was dissolved in methanol, and chloroform was added thereto, followed by performing centrifugation at 4,000 rpm for 5 minutes, thereby separating particles as a precipitate. This dissolution and the centrifugation were performed several times, so that unnecessary residual reagents were removed. The particles thus obtained were dried under reduced-pressure conditions and were then dissolved in ultrapure water, so that an aqueous solution of ZnS—ZAIS—SO$_3$H was obtained.

As ZnS—ZAIS—SO$_3$H used in the following toxicity test, the substance obtained in the synthetic example 2 was used.

B. Toxicity Test

Figure 2:
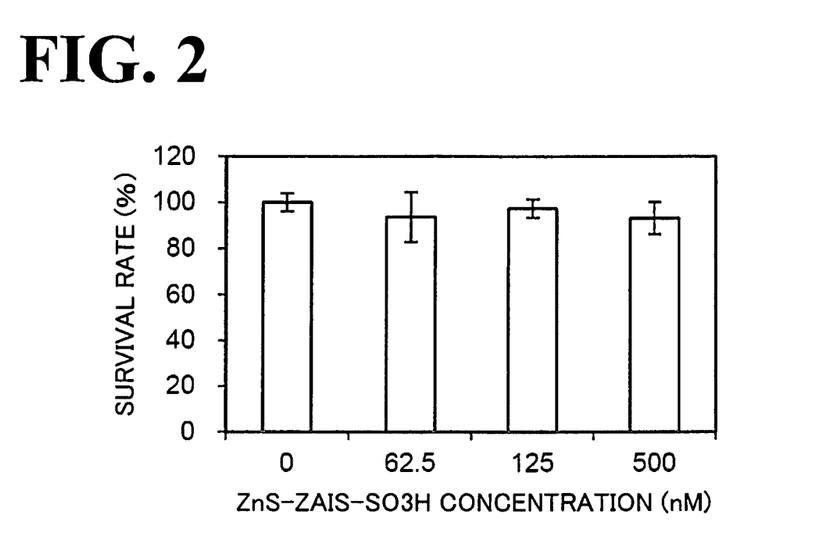
FIG. 2 is a graph showing the result of a toxicity test.
Figure 3:
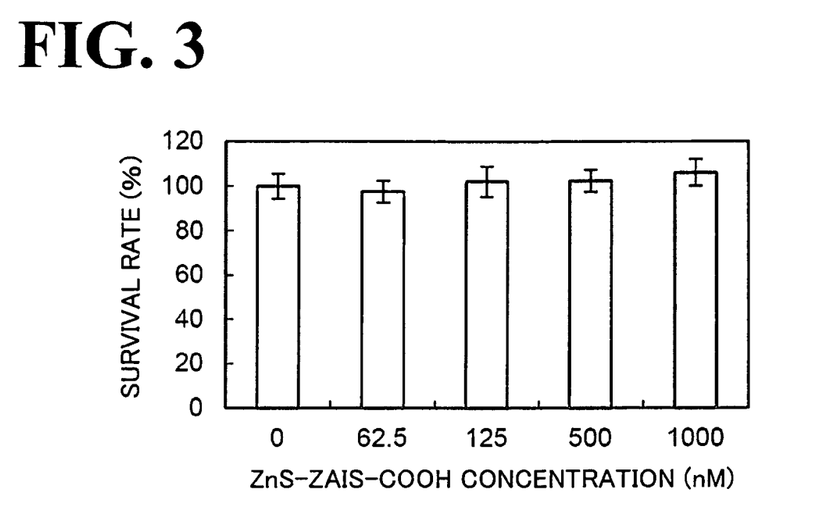
FIG. 3 is a graph showing the result of a toxicity test.

A toxicity test was performed as described below. By using a culture medium (FD medium: medium containing 50%/50% F12/DMEM+20% FBS+1% penicillin-streptomycin), mouse adipose tissue-derived stem cells (ASCs) were seeded in a 96-well plate at a density of $1 \times 10^4$ cells/well and were cultured in an incubator at 37° C. with 5% CO$_2$ for 24 hours. Subsequently, by using a maintenance medium (FD medium: medium containing 50%/50% F12/DMEM+2% FBS+1% penicillin-streptomycin), ZnS—ZAIS—SO$_3$H and ZnS—ZAIS—COOH were respectively conditioned and mixed with octa-arginine R8, which was a membrane permeable peptide, so as to have respective desired concentrations and were then allowed to stand still for 20 minutes. Next, the culture medium of ASCs was replaced with the conditioned ZnS—ZAIS—SO$_3$H solution or the conditioned ZnS—ZAIS—COOH solution, and the culture was then performed for 24 hours. The reason R8 was used is so as to enable ZnS—ZAIS—SO$_3$H or ZnS—ZAIS—COOH to be easily incorporated into cells. The number of cells was measured using an MIT assay, and the rate of the number of cells was calculated based on the number of cells of an additive-free cell group, the rate of which was regarded as 100%. The results are shown in FIGS. 2 and 3. As apparent from FIGS. 2 and 3, the cell toxicity was not observed even when the concentration of ZnS—ZAIS—SO$_3$H was 500 nM and the concentration of ZnS—ZAIS—COOH was 1,000 nM.

C. Proliferation Test

Figure 4:
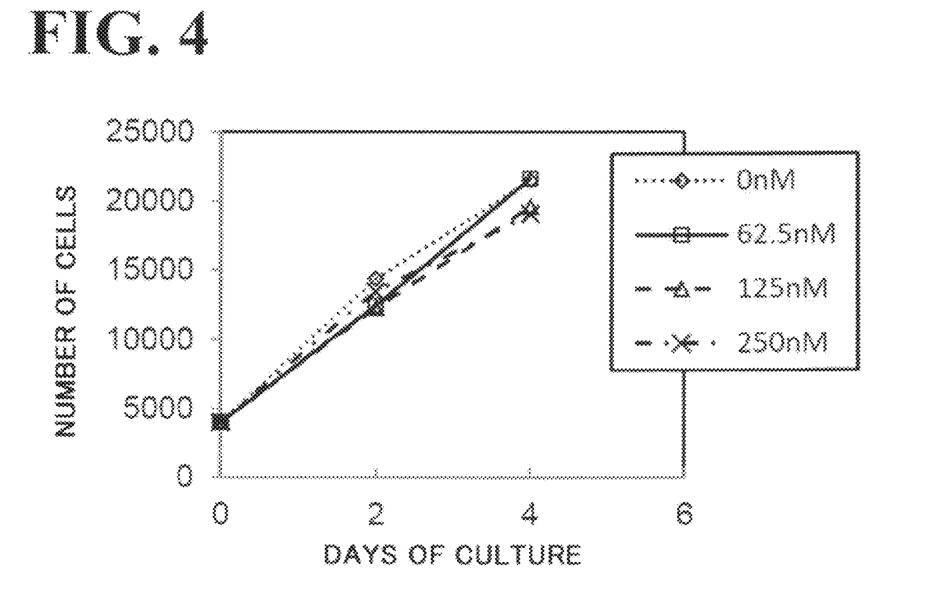
FIG. 4 is a graph showing the result of a proliferation test.

A proliferation test was performed as described below. By using the culture medium described above, ZnS—ZAIS—SO$_3$H and ZnS—ZAIS—COOH were conditioned to have respective desired concentrations, and ASCs were cultured for 4 hours by using the solution thus conditioned. Accordingly, ASCs was labeled by ZnS—ZAIS—SO$_3$H or ZnS—ZAIS—COOH. Subsequently, the culture medium was replaced with a general culture medium, and the labeled ASCs were cultured for 4 days. Next, the number of cell was measured by an MTT assay. The results of the ASCs labeled with ZnS—ZAIS—COOH are shown in FIG. 4. As apparent from FIG. 4, the ASCs labeled with ZnS—ZAIS—COOH proliferated at a growth rate similar to that of non-labeled ASCs. From these results described above, it was found that ZnS—ZAIS—COOH had no adverse influence on the cell proliferation.

D. Differentiation Induction Test

Figure 5:
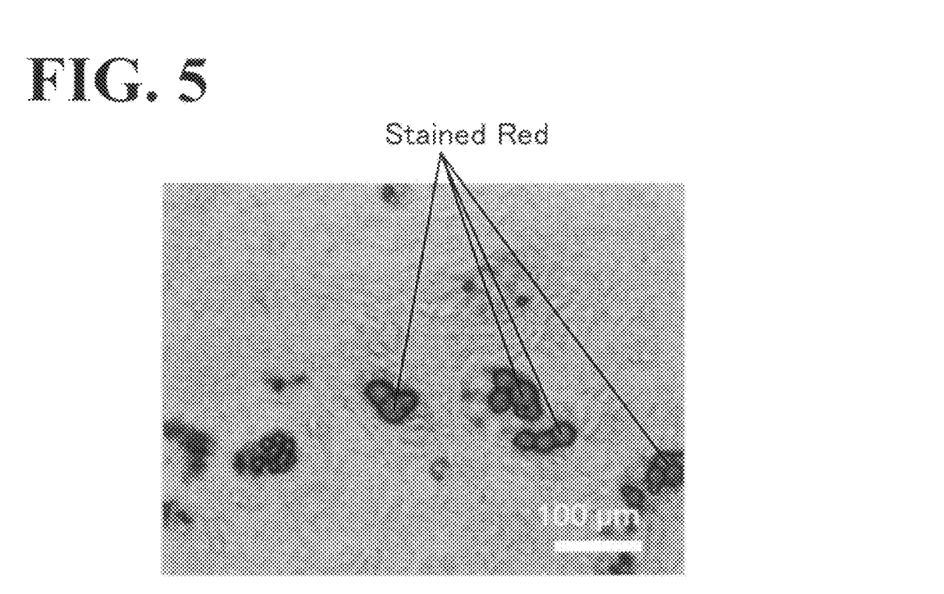
FIG. 5 is a photograph showing the result of a differentiation induction test.

To a DMEM medium, 0.5 mM 3-isobutyl-1-methylxanthine (L-6768, manufactured by Sigma-Aldrich), 1 μM dexamethasone (D-1756, manufactured by Sigma-Aldrich), 10 μM insulin (I-5500, manufactured by Sigma-Aldrich), and 10% FBS were added, so that an adipose tissue differentiation induction medium was prepared. In addition, 10% FBS was added to a DMEM medium, so that an adipose tissue culture medium was prepared. First, ASCs labeled with ZnS—ZAIS—COOH were added to the adipose tissue differentiation induction medium and were cultured for 3 days. The medium was replaced with a fresh differentiation induction medium 3 days after the induction, and the medium was then replaced with the adipose tissue culture medium 7 days after the induction. Furthermore, the medium was replaced with a fresh adipose tissue culture medium 10 days after the induction, and culture was further performed for 4 days. Subsequently, in order to confirm the adipose tissue differentiation, when oil red O staining was performed, red fat droplets were observed as shown in FIG. 5. Accordingly, by the differentiation induction of ASCs labeled with ZnS—ZAIS—COOH, it was confirmed that ASCs were differentiated into adipose tissues.

In addition, when ASCs labeled with ZnS—ZAIS—COOH were cultured without differentiation induction, no staining was observed by oil red O staining. Accordingly, it was also confirmed that ASCs which were only labeled were not differentiated into adipose tissues.

E. Cell Labeling

Figure 6:
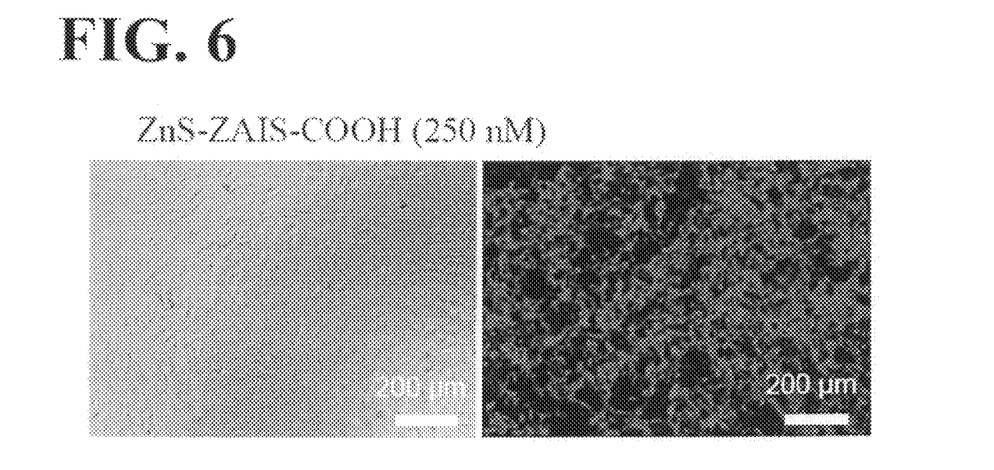
FIG. 6 includes photographs of cell labeling.
Figure 7:
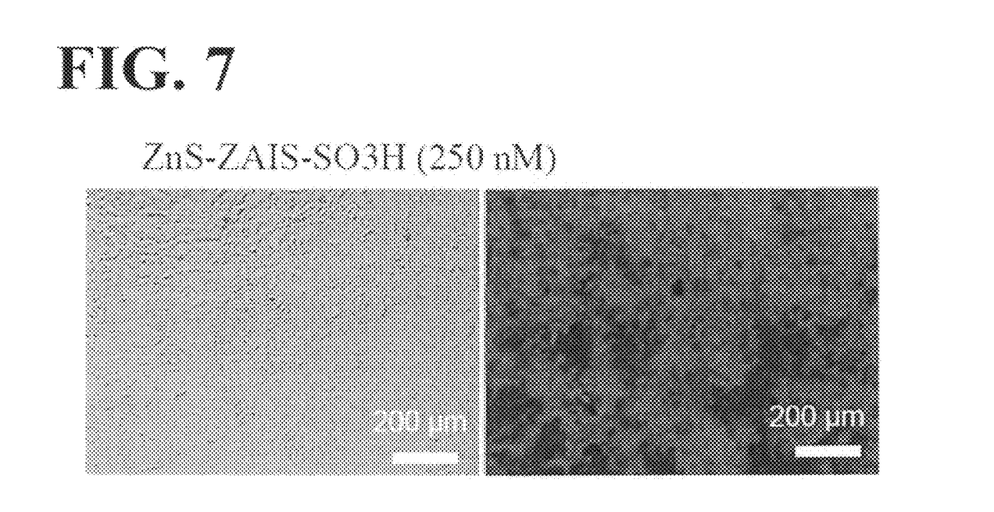
FIG. 7 includes photographs of cell labeling.

ASCs were labeled with ZnS—ZAIS—SO$_3$H and ZnS—ZAIS—COOH (concentration: 250 nM). FIG. 6 includes photographs of ASCs labeled with ZnS—ZAIS—COOH, (a) shows an optical microscopic image, and (b) shows a fluorescent microscopic image. In addition, FIG. 7 includes photographs of ASCs labeled with ZnS—ZAIS—SO$_3$H, (a) shows an optical microscopic image, and (b) shows a fluorescent microscopic image. Since cells emit red light in the fluorescent microscopic images of FIGS. 6 and 7, it is found that both ZnS—ZAIS—COOH and ZnS—ZAIS—SO$_3$H are effective for cell imaging.

F. Emission Quantum Yield

The emission quantum yield is represented by the rate of the number of photons emitted by light emission to the number of photons optically absorbed at room temperature. The measurement of the emission quantum yield was performed by an absolute quantum yield measurement apparatus using a sufficiently diluted ZnS—ZAIS chloroform solution or an aqueous solution of water-soluble ZnS—ZAIS nanoparticles (ZnS—ZAIS—SO$_3$H or ZnS—ZAIS—COOH). When ZnS—ZAIS was modified with 3-mercaptopropionic acid, the emission quantum yield at excitation light having a wavelength of 365 nm was changed from 47% to 30% (approximately 64% of the emission quantum yield before modification), and when ZnS—ZAIS was modified with 2-mercaptomethane sulfonic acid, the emission quantum yield as described above was changed from 58% to 35% (approximately 60% of the emission quantum yield before modification). In addition, the reason the emission quantum yield before modification varied as described above is because of the variation among lots. Compared to the case disclosed in NPL 2 in which when ZAIS was modified with 2-mercaptomethane sulfonic acid, the emission quantum yield was changed from 20% to 8% (approximately 40% of the emission quantum yield before modification), it is found that a decrease in emission quantum yield after the modification could be suppressed in the case of ZnS—ZAIS.

Figure 8:
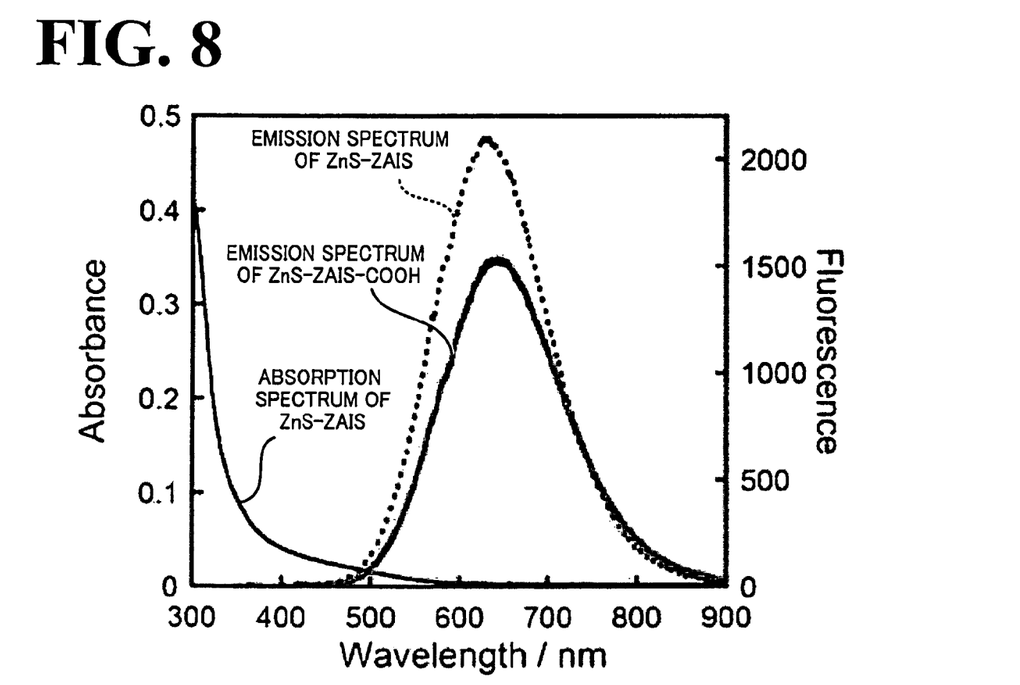
FIG. 8 is a graph showing one absorption spectrum and emission spectra.

Emission spectra obtained before and after ZnS—ZAIS was modified with 3-mercaptopropionic acid are shown in FIG. 8. In FIG. 8, an absorption spectrum of ZnS—ZAIS before modification is also shown. From FIG. 8, it is found that the peak wavelength of the emission spectrum obtained before the modification is not so much changed from that obtained after the modification. In addition, although being not shown, the emission spectrum of ZnS—ZAIS—SO$_3$H was approximately equivalent to that of ZnS—ZAIS—COOH, the emission wavelength region was approximately 500 to 900 nm, and the emission peak wavelength was approximately 650 nm.

Figure 9:
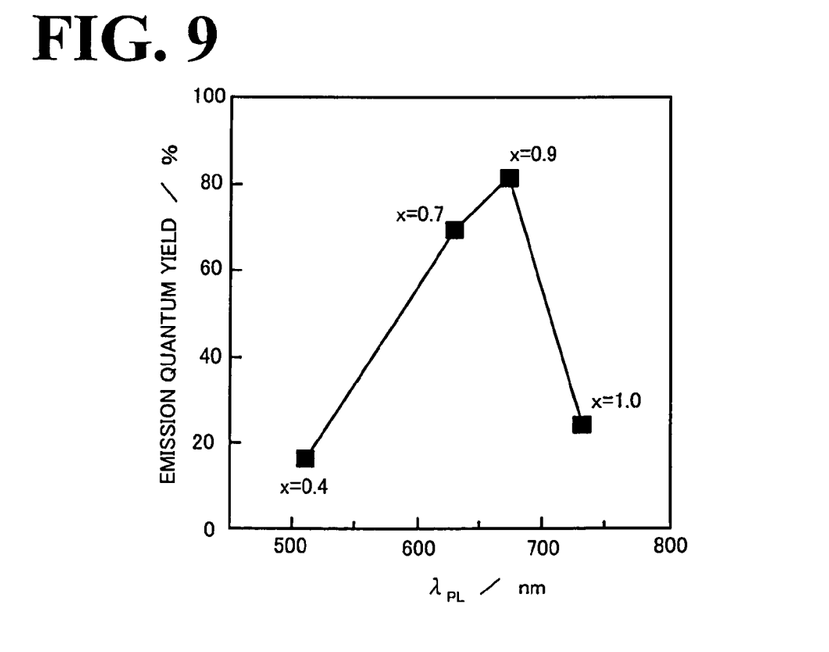
FIG. 9 is a graph showing the relationship between the emission quantum yield and the emission peak wavelength ($\lambda_{PL}$) of ZnS—ZAIS (x=0.4 to 1.0).

The relationship between the emission quantum yield and the emission peak wavelength ($\lambda_{PL}$) of ZnS—ZAIS (x=0.4 to 1.0) having no hydrophilic functional groups on a shell surface is shown in FIG. 9. Compared to the results shown in FIG. 8, it is found that the emission peak wavelength obtained when hydrophilic functional groups are present on the shell surface is almost equivalent to that obtained when no hydrophilic functional groups are present on the shell surface. In consideration of these results, in the case in which hydrophilic functional groups are present on the shell surface, it is also suggested that the relationship between the emission quantum yield and the emission peak wavelength ($\lambda_{PL}$) obtained when x=0.4 to 0.95 has the same tendency as that shown in FIG. 9. That is, in the semiconductor nanoparticles of the present invention, as long as x is in a range of 0.4 to 0.95, it is suggested that the emission quantum yield is relatively high.

G. Particle Diameter

Since the particle diameter of ZnS—ZAIS itself of the above 2. calculated from a TEM image was 3 to 4 nm, it is believed that in both cases of ZnS—ZAIS—SO$_3$H and ZnS—ZAIS—COOH, ZnS—ZAIS particles having a shell-core structure have the same particle diameter as ZnS—ZAIS itself.

H. Behavior in Aqueous Solution

Dynamic light scattering (DLS) measurement of a ZnS—ZAIS—SO$_3$H aqueous solution and that of a ZnS—ZAIS—COOH aqueous solution were performed. As a result, a peak having a maximum value at approximately 10 nm was obtained. From this result, it was confirmed that in each aqueous solution, the nanoparticles were preferably dispersed in an aqueous solution without being aggregated.

This application claims priority to Japanese Patent Application No. 2013-060365, filed on Mar. 22, 2013, which is hereby incorporated by reference herein in its entirety.

INDUSTRIAL APPLICABILITY

The present invention may be applied to quantum dots for cell imaging.

What is claimed is:

1. Semiconductor nanoparticles each having a core-shell structure that includes a core and a shell surrounding the core,
   wherein the core includes $(AgIn)_xZn_{2(1-x)}S_2$ (0.4≤x ≤0.95),
   the shell includes ZnS or ZnO, and
   the semiconductor nanoparticles each have a hydrophilic functional group on a surface of the shell.

2. The semiconductor nanoparticles according to claim 1, wherein 0.8≤x≤0.9.

3. A fluorescent probe for biological labeling, comprising: conductor nanoparticles according to claim 2.

4. The semiconductor nanoparticles according to claim 1, wherein the hydrophilic functional group is a carboxyl group or its salt or a sulfo group or its salt.

5. The semiconductor nanoparticles according to claim 4, wherein the hydrophilic functional group is a functional group of a bifunctional molecule having said hydrophilic functional group (first functional group) and a functional group (second functional group) which is bonded to the surface of the shell.

6. The semiconductor nanoparticles according to claim 5, wherein the second functional group contains a sulfur atom or a nitrogen atom.

7. The semiconductor nanoparticles according to claim 6, wherein the second functional group contains a sulfur atom and is a mercapto group; a group having a disulfide bond; a group having a sulfide bond; a pyridylthio group; or a dithiocarboxyl group.

8. A fluorescent probe for biological labeling, comprising: conductor nanoparticles according to claim 7.

9. The semiconductor nanoparticles according to claim 6, wherein the second functional group contains a nitrogen atom and is an imino group, an amide group, an imide group, or a pyridyl group.

10. A fluorescent probe for biological labeling, comprising:
conductor nanoparticles according to claim 9.

11. A fluorescent probe for biological labeling, comprising:
conductor nanoparticles according to claim 6.

12. The semiconductor nanoparticles according to claim 5, wherein the bifunctional molecule is 3-mercaptopropionic acid, 4-mercaptobutyric acid, 2-mercaptomethane sulfonic acid, 2-mercaptoethane sulfonic acid, 3-mercaptopropane sulfonic acid, or 2-mercaptoethane sodium sulfonate.

13. A fluorescent probe for biological labeling, comprising:
conductor nanoparticles according to claim 12.

14. A fluorescent probe for biological labeling, comprising:
conductor nanoparticles according to claim 5.

15. A fluorescent probe for biological labeling, comprising:
conductor nanoparticles according to claim 4.

16. A fluorescent probe for biological labeling, comprising:
the semiconductor nanoparticles according to claim 1.

* * * * *